US00PP14683P29

(12) United States Plant Patent
Knosher

(10) Patent No.: US PP14,683 P2
(45) Date of Patent: Apr. 6, 2004

(54) GAURA PLANT NAMED 'BALTINBLUS'

(50) Latin Name: *Gaura lindheimeri*
Varietal Denomination: Baltinblus

(75) Inventor: Lynne Knosher, St. Charles, IL (US)

(73) Assignee: Ball Horticultural Company, West Chicago, IL (US)

( * ) Notice: Subject to any disclaimer, the term of this patent is extended or adjusted under 35 U.S.C. 154(b) by 30 days.

(21) Appl. No.: 10/329,638

(22) Filed: Dec. 26, 2002

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—Wood, Phillips, Katz, Clark & Mortimer

(57) ABSTRACT

A new and distinct Gaura plant named 'Baltinblus', characterized by its blush pink flowers, upright slightly spreading growth habit, and dark green foliage.

2 Drawing Sheets

Latin name of genus and species of plant claimed: *Gaura lindheimeri.*
Variety denomination: 'Baltinblus'.

BACKGROUND OF INVENTION

The present invention comprises a new and distinct Gaura plant, botanically known as *Gaura lindheimeri*, and hereinafter referred to by the cultivar name 'Baltinblus'.

The new cultivar was developed by the inventor in a controlled breeding program during 1999, at Elburn, Ill. The objective of the breeding program was the development of Gaura cultivars with a well-branched, compact habit, continuous flowering and dark green foliage.

The female (seed) parent of 'Baltinblus' was the commercially available Gaura variety 'Siskyou Pink' (not patented) characterized by its medium pink flowers. The male (pollen) parent of 'Baltinblus' was an unnamed white dwarf Japanese Gaura variety which exhibits an upright habit and white flowers. Protection status of the male parent is unknown to the inventor.

'Baltinblus' was selected in August 2000 as a single flowering plant from within the progeny of the above stated cross and was initially designated '0019-A3'.

Asexual reproduction of the new cultivar at West Chicago, Ill. was carried out by the use of terminal stem cuttings has demonstrated that the Gaura reproduces true to type with the characteristics as herein described are firmly fixed and retained through successive generations of such asexual propagation.

SUMMARY OF INVENTION

It was found that the cultivar of the present invention:

(a) exhibits blush pink colored flowers, (b) forms foliage of a dark green color, and (c) exhibits an upright and slightly spreading growth habit.

The new cultivar of the present invention can be compared to its female parent, the commercially available Gaura variety, 'Siskiyou Pink'. In side-by-side comparison, plants of the new cultivar have fewer flowering branches and smaller leaves than plants of 'Siskiyou Pink'.

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown in 10 cm pots for 13 weeks in a greenhouse at West Chicago, Ill.

DETAILED BOTANICAL DESCRIPTION

Figure 1:
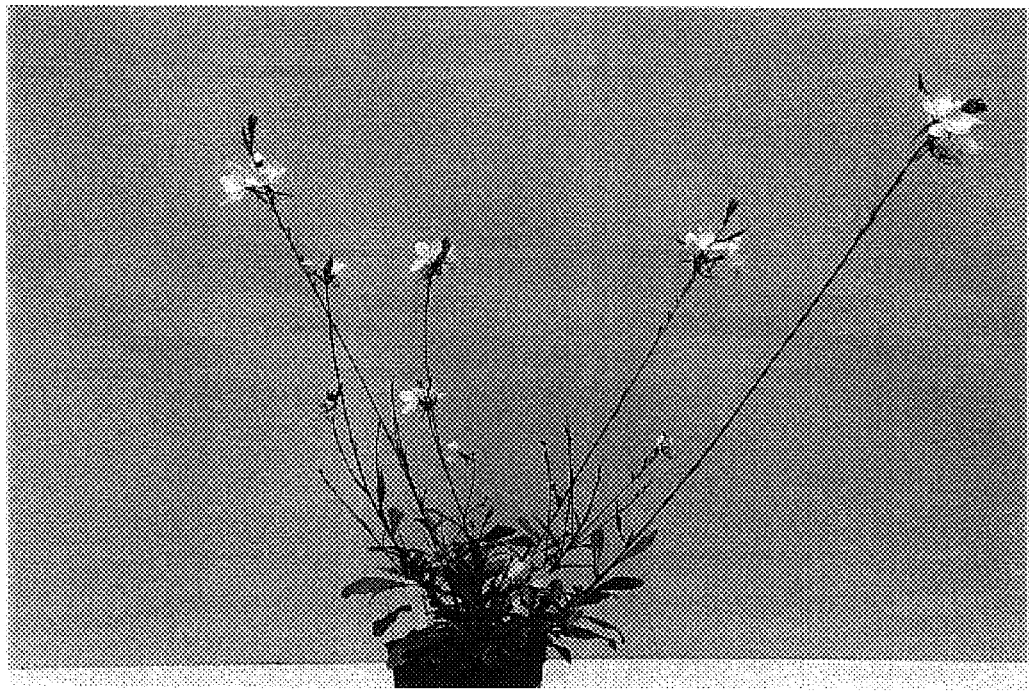
FIG. 1 illustrates the typical growth habit and flower color for 'Baltinblus'.
Figure 2:
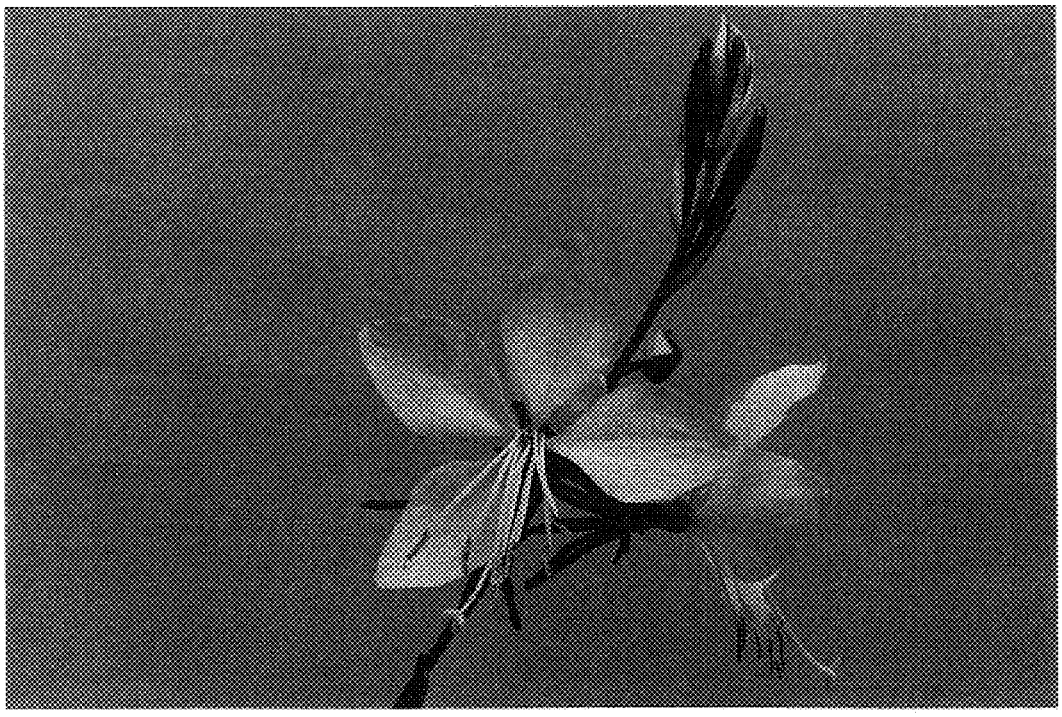
FIG. 2 illustrates a close up view of individual flowers of 'Baltinblus'.

The new cultivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 15, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown for 12 weeks while utilizing a soilless growth medium and maintaining temperatures of approximately 70° to 75° F. (21° to 24° C.) during the day and approximately 55° to 60° F. (13° to 15° C.) during the night and light levels of 5,000 to 9,000 footcandles.

Classification:
*Botanical.*—*Gaura lindheimeri* cultivar 'Baltinblus'.
Parentage:
*Female parent.*—'Siskyou Pink'.
*Male parent.*—Unnamed dwarf Japanese Gaura variety.
Propagation:
*Type cutting.*—Terminal tip.
*Time to initiate roots.*—Approximately 14 to 21 days.
*Root description.*—Fibrous, branching.
Plant description:
*Habit of growth.*—Moderately vigorous. The foliage of a mature plant, 12 weeks after the planting of a rooted cutting, measures approximately 20 cm in height and approximately 25.2 cm in width with 7.2 flowering branches.

*Form.*—Upright.

*Stem.*—Approximately 59.7 cm in length and 3 mm in diameter, with moderate amount of short stiff hairs. Color is 138A with overlay of 185A.

*Foliage.*—Leaves are simple, alternate, oblanceolate with dentate margin, acute apex and attenuate sessile base. Upper and lower surfaces are densely covered with short, stiff hairs. Leaf length is approximately 6 cm and width is approximately 1.2 cm. Upper surface of mature foliage is darker than 137A and lower surface is 137A. Upper and lower surfaces have venation of 143C.

Inflorescence description:

*Type.*—Spicate racemes.

*Length.*—Approximately 15 cm.

*Diameter.*—Approximately 8 cm.

*Number of flowers per raceme.*—Approximately 3.

Flowering description:

*Flowering habit.*—Freely flowering.

*Natural flowering season.*—Year round in greenhouse environment and spring through autumn in outdoor garden.

Flower description:

*Fragrance.*—Light, sweet.

*Lastingness of bloom.*—Approximately 3 days.

*Shape.*—Round. Length: Approximately 2.4 cm. Width: Approximately 4.1 cm. Depth: Approximately 7 mm.

*Pedicel.*—Length is approximately 6 mm and diameter is approximately 1 mm. Aspect: At an acute angle to branch. Texture: Pubescent with short, stiff hairs. Color: 176B.

*Corolla.*—Width: Approximately 4.1 cm. Length: Approximately 2.4 cm. Depth: Approximately 7 mm.

*Petals.*—Five, non-overlapping. Shape: Oblanceolate. Length: 2.1 cm. Width: 1.2 cm. Apex: Acute. Base: Attenuate. Margin: Entire. When fully open, the upper and lower surfaces are 65C with venation of 65A. There is a small area of 67B at the base of each petal. Upper and lower surfaces of petals are smooth.

*Bud.*—Cigar shaped, approximately 1.3 cm in length, 60A when closed and between 65A and 65B at first opening. Diameter: Approximately 2.2 mm.

*Sepal.*—Quantity: 4. Lanceolate in shape, fused at tip until flower fully opens. Approximately 2 cm in length, 1 mm in width with acute apex and entire margin. Upper surface of sepals is moderately pubescent. Lower surface has no pubescence. Upper and lower surfaces are 60B with 143A at tip.

*Bract.*—Number per flower: Two. Shape: Lanceolate. Length: 1 cm. Diameter: 2 mm. Apex: Acuminate. Base: Truncate. Margin: Entire. Color — upper and lower: 145D.

*Reproductive organs.*—There are 8 stamens. Stamen length: 1.2 cm. Stamen color: Closest to 65C. Anther length: 3 mm. Anther color: 187A. Pollen amount: Sparse. Pollen color: 4C. There is one pistil, 2.1 cm in length. Stigma length: Approximately 3 mm. Stigma color 2D. Style length: Approximately 1.5 cm. Style color: 67C at base and apex and 65C in mid portion. Ovary length: Approximately 6 mm. Ovary color: 60A.

Seed production: Seed production has not been observed.

Disease resistance: Resistance to pathogens has not been observed.

Hardiness zone: 'Baltinblus' is hardy in zones nine (9) and above.

I claim:

1. A new and distinct *Gaura lindheimeri* plant named 'Baltinblus' substantially as herein shown and described, which:

(a) exhibits blush pink colored flowers, (b) forms dark green foliage, and (c) exhibits an upright and slightly spreading growth habit.

* * * * *